United States Patent [19]

Jung et al.

[11] Patent Number: 5,726,264
[45] Date of Patent: Mar. 10, 1998

[54] PROCESSES TO PRODUCE METALLOCENE COMPOUNDS AND POLYMERIZATION PROCESSES THEREWITH

[75] Inventors: Michael Jung; Helmut G. Alt, both of Bayreuth, Germany; M. Bruce Welch, Bartlesville, Okla.

[73] Assignee: Phillips Petroleum Company, Bartlesville, Okla.

[21] Appl. No.: 663,885

[22] Filed: Jun. 14, 1996

[51] Int. Cl.$^6$ .................. C08F 4/68; C08F 4/64; C08F 4/69

[52] U.S. Cl. .................. 526/170; 526/160; 526/308; 526/281; 526/348.3; 526/348.4; 526/348.5; 526/348.6; 526/335; 526/346; 556/43; 556/53; 556/58; 502/108; 502/152; 260/665 R

[58] Field of Search ..................... 526/160, 170, 526/943, 348.3, 348.4, 348.5, 348.6; 556/43, 53, 58; 502/108, 152, 111; 260/665 R

[56] References Cited

U.S. PATENT DOCUMENTS

| | | | |
|---|---|---|---|
| 5,087,677 | 2/1992 | Brekner et al. | 526/160 |
| 5,406,013 | 4/1995 | Patsidis et al. | 585/375 |
| 5,565,592 | 10/1996 | Patsidis et al. | 526/943 X |
| 5,594,078 | 1/1997 | Welch et al. | 526/904 X |

OTHER PUBLICATIONS

Rieger et al., Bernhard, *Chem. Ber.* "Chiral Epoxides as Building Blocks for Ethylene–Bridged ansa–Mettalocene Complexes—Synthesis of $C_1$-Symmetrical Zirconocene Dichlorides with Two Different Cyclopentadienyl Units", (1992), 125, pp. 2373–2377.

Rieger et al., Bernhard, *Organometallics* "Unsymmetric ansa–Zirconocene Complexes with Chiral Ethylene Bridges: Influence of Bridge Conformation and Monomer Concentration on the Stereoselectivity of the Propene Polymerization Reaction", (1994), 13, pp. 647–653.

*Primary Examiner*—Fred Teskin
*Attorney, Agent, or Firm*—Carl D. Corvin

[57] ABSTRACT

A process to produce an ethylene-bridged-metallocene-transition-metal compound that has an omega-alkenyl substitution on said ethylene bridge is provided. Said process comprises: contacting a diolefin compound with a peracid compound to form an omega-alkenyl oxirane compound; contacting said omega-alkenyl oxirane compound with an organometal compound to form an organo-omega-alkenyl-alcohol compound; contacting said organo-omega-alkenyl-alcohol compound with an organosulfur compound to form an organo-omega-alkenyl-organosulfur ester compound; contacting said organo-omega-alkenyl-organosulfur ester compound with an organometal to form an orgaomega-alkenyl-organo compound; contacting said organo-omega-alkenyl-organo compound with a transition metal compound to form a organo-omega-alkenyl-organo-transition compound. Additionally, processes to polymerize olefins using these compounds is provided.

10 Claims, No Drawings

PROCESSES TO PRODUCE METALLOCENE COMPOUNDS AND POLYMERIZATION PROCESSES THEREWITH

This invention is related to the field of metallocene compounds. In particular, it is related to processes to produce ethylene-bridged-metallocene-transition-metal-compounds that have omega-alkenyl substitution on the ethylene bridge and processes to use such compounds to polymerize olefins.

BACKGROUND OF THE INVENTION

Since the discovery of ferrocene about 45 years ago, a number of metallocene compounds have been prepared by combining: (1) compounds having a cyclopentadienyl group; and (2) compounds having a transition metal. However, processes to produce these types of compounds are not entirely satisfactory. Consequently, new processes are being searched for that provide advantages in producing these metallocene compounds.

SUMMARY OF THE INVENTION

It is an object of this invention to provide processes to produce metallocene compounds and processes to use such compounds to polymerize olefins.

It is another object of this invention to provide a process to produce ethylene-bridged-metalocene-transition-metal compounds that have omega-alkenyl substitution on the ethylene bridge and processes to use such compounds to polymerize olefins.

In accordance with this invention, a process to produce an ethylene-bridged-metallocene-transition-metal compound that has an omega-alkenyl substitution on said ethylene bridge is provided. Said process comprises:

(a) contacting a diolefin compound with a peracid compound to form an omega-alkenyl oxirane compound;

(b) contacting said omega-alkenyl oxirane compound with an organometal compound to form an organo-omega-alkenyl-alcohol compound;

(c) contacting said organo-omega-alkenyl-alcohol compound with an organosulfur compound to form an organo-omega-alkenyl-organosulfur ester compound;

(d) contacting said organo-omega-alkenyl-organosulfur ester compound with an organometal to form an organo-omega-alkenyl-organo compound;

(e) contacting said organo-omega-alkenyl-organo compound with a transition metal compound to form a organo-omega-alkenyl-organo-transition metal compound.

Additionally, processes to polymerize olefins using these compounds is provided.

These and other objects will become better understood by those skilled in the art by reviewing the following disclosure.

DETAILED DESCRIPTION OF THE INVENTION

The first step in the inventive process is to contact a diolefin compound with a peracid compound to form an omega-alkenyl oxirane compound.

The diolefin compounds useful in this invention are those diolefin compounds that have the following formula.

Formula One

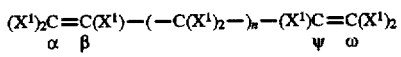

In Formula One "$X^1$" can be hydrogen, or any other substituent that does not substantially interfere with the reactivity of the carbon-carbon double bonds located between the alpha-beta and the psi-omega carbon atoms. Suitable examples of such substituents include, but are not limited to, hydrocarbyl radicals such as, for example, alkyl, aryl, and alkylaryl radicals. Also, in Formula One "n" can be any integer from 1 to about 20. Suitable examples of compounds that fall within Formula One include, but are not limited to, 1,3 butadiene, 1,4 pentadiene, 1,5 hexadiene, 1,6 heptadiene, 1,7 octadiene, 1,8 nonadiene, 1,9 decadiene, and 5-methyl-1,7-octadiene. Mixtures of these compounds can also be used.

The peracid compounds useful in this invention are those peracid compounds that have the following formula.

Formula Two $$R^1-CO_3H$$

In Formula Two "$R^1$" is a hydrogen, or a hydrocarbyl radical that has from 1 to about 50 carbon atoms. Suitable examples of such hydrocarbyl radicals are for example, alkyl, aryl, arylalkyl. These hydrocarbyl radicals can be substituted or unsubstituted. An example of a suitable compound is meta-chloroperbenzoic acid.

The omega-alkenyl oxirane compounds produced at this step have the following formula.

Formula Three

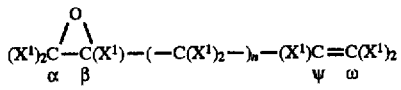

In Formula Three, "$X^1$" and "n" are as before.

The contacting, in this first step, can be conducted at any suitable temperature and pressure. Currently, a temperature of about $-80°$ C. to about $200°$ C. and a pressure of about 0 Pa to about $4 \times 10^6$ Pa are preferred. However, a temperature of about $0°$ C. to about $50°$ C. and a pressure of about 0 Pa to about $1 \times 10^5$ Pa are preferred. The molar ratio of the diolefin compound to the peracid compound can be any suitable ratio. Currently, molar ratios from $1:1 \times 10^6$ to $1 \times 10^6:1$ are preferred.

The second step in this inventive process is to contact said omega-alkenyl oxirane compound with an organometal compound to form an organo-omega-alkenyl-alcohol compound.

The organometal compounds useful in this invention are those organometal compounds that have the following formula.

Formula Four $$Cp^1-M^1$$

In Formula Four, $Cp^1$ stands for an organoradical that has a cyclopentadienyl group and $M^1$ stands for a Group IA metal radical. Suitable examples of organoradicals include, but are not limited to, unsubstituted or substituted cyclopentadienyl radicals, unsubstituted or substituted indenyl radicals, unsubstituted or substituted fluorenyl radicals, and unsubstituted or substituted tetrahydroindenyl radicals. The substituents on the organoradical can include hydrocarbyl groups containing 1 to 12 carbon atoms, alkoxy groups containing 1 to 12 carbon atoms, trialkylsilyl groups where each alkyl contains 1 to 12 carbon atoms, alkyl halide groups where the alkyl contains 1 to 12 carbon atoms, or halide. Preferably the substituents containing alkyl groups contain 1 to 10 carbon atoms, more preferably 1 to 6 carbon atoms. Some examples of substituents include methyl, ethyl, propyl, butyl, tert-butyl, isobutyl, amyl, isoamyl, hexyl, cyclohexyl, heptyl, octyl, nonyl, decyl, dodecyl, 2-ethylhexyl, pentenyl, butenyl, phenyl, chloride, bromide, and iodide. Currently, lithium is the preferred Group IA metal. Suitable examples of organometal compounds include, but are not limited to, fluorenyllithium, cyclopentadienyllithium, 1-methylindenyllithium, and indenyllithium.

The organo-omega-alkenyl-alcohol compounds produced at this step have the following formula.

Formula Five

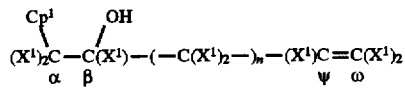

In Formula Four, "$X^1$"; "n"; and "$Cp^1$" are as before.

The contacting, in this second step, can be conducted at any suitable temperature and pressure. Currently, a temperature of about −80° C. to about 200° C. and a pressure of about 0 Pa to about 4×10⁶ Pa are preferred. However, a temperature of about 0° C. to about 50° C. and a pressure of about 0 Pa to about 2×10⁵ Pa are preferred. The molar ratio of the omega-alkenyl oxirane compound to the organometal compound can be any suitable ratio. Currently, molar ratios from 1:1×10⁶ to 1×10⁶:1 are preferred.

The third step in this inventive process is to contact said organo-omega-alkenyl-alcohol compound with an organosulfur compound to form an organo-omega-alkenyl-organosulfur ester compound.

The organosulfur compounds useful in this invention are those organosulfur compounds that have one of the following formulas.

Formula Six $$R^2SO_2X^2$$

In Formula Six, $R^2$ is a hydrocarbyl radical having from 1 to 20 carbon atoms, preferably a methyl radical, and $X^2$ is a halogen, preferably chloride. The hydrocarbyl radical can be substituted or unsubstituted with, for example, other hydrocarbyl radicals and/or halides. Suitable examples include, but are not limited to, methanesulfonyl chloride (also known as "mesyl chloride") and trifluoromethanesulfonyl chloride. Further information concerning these types of reactions can be found in "The Facile Synthesis of Methanesulfonate Esters" by Crossland, R. K. and Servis K. L. in J. Org. Chem., Vol 35, No.9, 1970 pages 3195-3196 (the disclosure of which is hereby incorporated by reference).

The organo-omega-alkenyl-organosulfur ester compounds produced at this step have the following formula.

Formula Seven

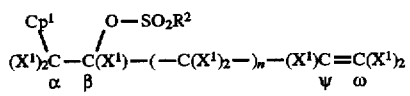

In Formula Seven, "$X^1$"; "n"; "$Cp^1$"; and "$R^2$" are as before.

The contacting, in this third step, can be conducted at any suitable temperature and pressure. Currently, a temperature of about −80° C. to about 200° C. and a pressure of about 0 Pa to about 4×10⁶ Pa are preferred. However, a temperature of about 0° C. to about 50° C. and a pressure of about 0 Pa to about 2×10⁵ Pa are preferred. The molar ratio of the organo-omega-alkenyl-alcohol compound to the organosulfur compound can be any suitable ratio. Currently, molar ratios from 1:1×10⁶ to 1×10⁶:1 are preferred. Additionally, this contacting should be conducted in the presence of a weak base which can remove the acidic hydrogen from the alcohol portion of the organo-omega-alkenyl-alcohol compound. A suitable example of a weak base is triethylamine.

The fourth step in this inventive process is to contact said organo-omega-alkenyl-organosulfur ester compound with an organometal compound to form an organo-omega-alkenyl-organo compound.

The organometal compounds useful in this invention are those organometal compounds that have the following formula.

Formula Eight $$Cp^2 — M^2$$

In Formula Eight, $Cp^2$ stands for an organoradical that has a cyclopentadienyl group and $M^2$ stands for a Group IA metal radical. Suitable examples of organoradicals include, but are not limited to, unsubstituted or substituted cyclopentadienyl radicals, unsubstituted or substituted indenyl radicals, unsubstituted or substituted fluorenyl radicals, and unsubstituted or substituted tetrahydroindenyl radicals. The substituents on the organoradical can include hydrocarbyl groups containing 1 to 12 carbon atoms, alkoxy groups containing 1 to 12 carbon atoms, trialkylsilyl groups where each alkyl contains 1 to 12 carbon atoms, alkyl halide groups where the alkyl contains 1 to 12 carbon atoms, or halide. Preferably the substituents containing alkyl groups contain 1 to 10 carbon atoms, more preferably 1 to 6 carbon atoms. Some examples of substituents include methyl, ethyl, propyl, butyl, tert-butyl, isobutyl, amyl, isoamyl, hexyl, cyclohexyl, heptyl, octyl, nonyl, decyl, dodecyl, 2-ethylhexyl, pentenyl, butenyl, phenyl, chloride, bromide, and iodide. Currently, lithium is the preferred Group IA metal. Suitable examples of organometal compounds include, but are not limited to, fluorenyllithium, cyclopentadienyllithium, 1-methylindenyllithium, and indenyllithium.

The organo-omega-alkenyl-organo compounds produced at this step have the following formula.

Formula Nine

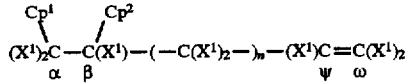

In Formula Nine, "$X^1$"; "n"; "$Cp^1$"; "$R^2$"; and "$Cp^2$" are as before.

The contacting, in this fourth step, can be conducted at any suitable temperature and pressure. Currently, a temperature of about −80° C. to about 200° C. and a pressure of about 0 Pa to about 4×10$^6$ Pa are preferred. However, a temperature of about 0° C. to about 50° C. and a pressure of about 0 Pa to about 2×10$^5$ Pa are preferred. The molar ratio of the organo-omega-alkenyl-organosulfur ester compound to the organometal compound can be any suitable ratio. Currently, molar ratios from 1:1×10$^6$ to 1×10$^6$:1 are preferred.

The fifth step in this inventive process is to contact said organo-omega-alkenyl-organo compound with an transition metal compound to form an organo-omega-alkenyl-organo-transition-metal compound.

The transition metal compound useful in this invention are those transition metal compounds that have the following formula.

Formula Ten

In Formula Ten, $M^3$ is selected from the transition metals of Groups IVB, VB, and VIB, and $X^3$ represents a halogen atom or an organo group, and m is the valence state of the transition metal, preferably four. Examples of the transition metals thus include zirconium, titanium, hafnium, chromium and vanadium. Some illustrative examples of such transition metal compounds include vanadium dichloride, vanadium trichloride, vanadium tetrachloride, vanadium pentafluoride, vanadium triiodide, titanium dibromide, titanium tetrachloride, titanium trichloride, titanium tetrafluoride, titanium tetraiodide, titanium tetrabromide, zirconium trichloride, zirconium tetrachloride, zirconium tetrabromide, zirconium tetraiodide, zirconium tetrafluoride, $Zr(NH_2)_4$, $Zr(NI(CH_2CH_3)_2)_4$, $Zr(N(CH_2CH_3)_2)_2Cl_2$, hafnium trichloride, hafnium tetrachloride, hafnium tetrabromide, hafnium tetraiodide, hafnium tetrafluoride, $Hf(NH_2)_4$, $Hf(N(CH_2CH_3)_2)_4$, $Hf(N(CH_2CH_3)_2)_2Cl_2$, chromic chloride, titanium tetraethoxide, titanium tetrabutoxide, zirconium tetrabutoxide, dicyclopentadienyl titanium dichloride, dicyclopentadienyl zirconium dichloride, and the like.

The organo-omega-alkenyl-organo-transition-metal compounds produced at this step have the following formula.

Formula Eleven

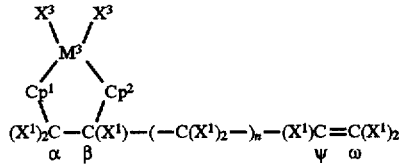

In Formula Eleven, "$X^1$"; "n"; "$Cp^1$"; "$R^2$"; "$Cp^2$"; "$M^3$"; and "$X^3$" are as before.

The contacting, in this fifth step, can be conducted at any suitable temperature and pressure. Currently, a temperature of about −80° C. to about 200° C. and a pressure of about 0 Pa to about 4×10$^6$ Pa are preferred. However, a temperature of about 0° C. to about 50° C. and a pressure of about 0 Pa to about 2×10$^5$ Pa are preferred. The molar ratio of the organo-omega-alkenyl-organo compound to the transition metal compound can be any suitable ratio. Currently, molar ratios from 1:1×10$^6$ to 1×10$^6$:1 are preferred. Additionally, this contacting should be conducted in the presence of an organometal compound which can form a metal salt compound of the organo-omega-alkenyl-organo compound thereby promoting the formation of the organo-omega-alkenyl-organo-transition metal compound. Suitable examples of organometals compounds include, but are not limited to the alkyl-Group IA compounds, such as, for example butyl lithium, butyl sodium, butyl potassium, and pentyl lithium.

These organo-omega-alkenyl-organotransition-metal compounds can be used to polymerize various olefins. The particular polymerization conditions employed using these compounds can vary depending upon the particular results desired. Usually these compounds are used with organoaluminoxane compounds, such as, for example, methylaluminoxane, to form better polymerization catalysts. These organoaluminoxane compounds can be soluble or insoluble in the polymerization medium. The ratio of the transition metal to the organo-aluminoxane composition can vary widely depending upon the particularcomposition selected and the results desired. Typically, the atomic ratio of aluminum in the organo-aluminoxane composition to the transition metal is in the range of about 1/1 to about 5000/1, preferably about 15/1 to about 1000/1, and more preferably about 100/1 to about 1000/1.

Examples of some monomers for polymerization include ethylene and alpha-olefins having 3 to 20 carbon atoms, such as propylene, 1-butene, 3-methyl- 1-butene, 3-methyl-1-pentene, 3 ethylene-1-hexene, 1-hexene, 4-methyl -1-pentene, 1-octene, 1-hexadecene, cyclopentene, norborene, styrene, 4-methyl styrene, vinyl cyclohexane, butadiene, and the like and mixtures thereof.

The present invention is particularly useful in slurry type polymerizations since it allows one to carry out such polymerizations more effectively than has heretofore been possible. A particularly preferred type of slurry polymerization involves the continuous loop reactor type polymerization wherein monomer, feed, catalyst, and diluent, if employed, are continuously added to the reactor as needed and polymer product is continuously or at least periodically removed. Generally in such processes, ethylene is polymerized in the presence of a suitable liquid diluent, a higher alpha-olefin comonomer, and optionally, hydrogen. The polymerization temperature can vary over the range which will allow for slurry polymerization. Often the slurry polymerization would be conducted at a temperature in the range of about 60° C. to about 100 ° C., although higher and lower temperatures can be used.

The following examples were provided to further illustrate this invention. However, the invention should not be construed to be limited to these examples.

EXAMPLES

All examples were carried out using standard Schlenk techniques with the exclusion of oxygen and air moisture under argon. The solvents were dried over either: (a) Na/K alloy for ether, hexane, pentane, tetrahydrofuran, and toluene; (b) $P_{4I0}$ for methylene chloride; or (c) magnesium for methanol; and then distilled under argon.

EXAMPLE ONE: PREPARATION OF OMEGA-ALKENYL OXIRANE COMPOUNDS

In this example, alpha-omega diolefins are reacted with per-acids to form omega-alkenyl oxiranes.

PART A: PREPARATION OF OMEGA-BUTENYL OXIRANE 13.75 g (79.6 mool) m-chloroperbenzoic acid, which was in 250 mL methylene chloride, was added dropwise to a solution of 9 g (110 mmol) 1,5-hexadiene, which was also in 200 mL methylene chloride, and this mixture was stirred overnight. The suspension that formed was filtered off and then washed with 2M NaHCO₃, 2N KOH, and water. The organic phase was dried over sodium sulfate and the solvent was then evaporated. The residue was distilled to yield omega-butenyl oxirane, which had a b.p. 119°–121° C.

PART B: PREPARATION OF OMEGA-HEXENYL OXIRANE 13.81 g (80 mol) m-chloroperbenzoic acid, which was in 250 mL methylene chloride, was added dropwise to a solution of 8.82 g (80 mmol) 1,7-octadiene, which was also, in 200 mL methylene chloride, and this mixture was stirred overnight. The suspension that formed was filtered off and then washed with 2M NaHCO₃, 2N KOH, and water. The organic phase was dried over sodium sulfate and the solvent was then evaporated. The residue was distilled to yield omega-hexenyl oxirane, which had a b.p. 146°–150 ° C.

PART C: PREPARATION OF OMEGA-DECENYL OXIRANE 33.3 g (100 mmol) m-chloroperbenzoic acid, which was in 250 mL methylene chloride, was added dropwise to a solution of 18.7 g (135 mmol) 1,9-decadiene, which was also in 200 mL methylene chloride, and this mixture was stirred overnight. The suspension that formed was filtered off and then washed with 2M NaHCO₃, 2N KOH, and water. The organic phase was dried over sodium sulfate and the solvent was then evaporated. The residue was distilled to yield omega-decenyl oxirane, which had a b.p. 75°–80° C.

EXAMPLE TWO: PREPARATION OF ORGANO-OMEGA-ALKENYL-ALCOHOL COMPOUNDS

In this example, the omega-alkenyl oxiranes produced in Example One, are reacted with fluorenyllithium to form 1-fluorenyl-omega-alkenyl-2-ol.

PART A: PREPARATION OF 1-FLUORENYL-OMEGA-HEXENYL-2-OL 61.1 mmol of omega-butenyl oxirane are added at –78° C. to a suspension containing 61.1 mmol fluorenyllithium suspended in 100 mL diethyl ether. The resulting mixture is then stirred overnight. This mixture was then washed with NH₄Cl/H₂O. This was followed by having the organic phase evaporated, thus obtaining 1-fluorenyl-hex-5-en-2-ol.

PART B: PREPARATION OF 1-FLUORENYL-OMEGA-OCTENYL-2-OL 61.1 mmol of omega-hexenyl oxirane are added at –78° C. to a suspension containing 61.1 mmol fluorenyllithium suspended in 100 mL diethyl ether. The resulting mixture is then stirred overnight. This mixture was then washed with NH₄Cl/H₂O. This was followed by having the organic phase evaporated, thus obtaining 1-fluorenyl-7-en-2-ol.

PART C: PREPARATION OF 1-FLUORENYL-OMEGA-DECENYL-2-OL 23.6 mmol of omega-hexenyl oxirane are added at –78° C. to a suspension containing 23.6 mmol fluorenyllithium suspended in 100 mL diethyl ether. The resulting mixture is then stirred overnight. This mixture was then washed with NH₄Cl/H₂C). This was followed by having the organic phase evaporated, thus obtaining 1-fluorenyl-dec-9-en-2-ol.

EXAMPLE THREE: PREPARATION OF ORGANO-OMEGA-ALKENYL-ORGANOSULFUR ESTER COMPOUNDS

In this example, the 1-fluorenyl-omega-alkenyl-2-ols produced in Example Two, are reacted with methanesulfonyl chloride (hereafter "mesyl chloride") to produce 1-fluorenyl-omega-alkenyl-2-mesylates.

PART A: PREPARATION OF 1-FLUORENYL-OMEGA-HEXENYL-2-MESYLATE

To a solution of 16.1 g (61 mmol) of 1-fluorenylhex-5-en-2-ol in 100 mL of methylene chloride, which also contains 13.91 mL (100 mmol) triethylamine, and which was at a temperature of about –40° to –50° C., was added 7.56 g (66 mmol) of mesyl chloride over a period of about 15 minutes. The resulting mixture was then stirred for about 15 minutes without further cooling. This mixture was then extracted with ice water, followed by cold 10 percent hydrochloric acid and cold sodium bicarbonate solution. The organic layer was then dried over Na₂SO₄ and the organic phase was removed to obtain 1-fluorenyl-hex-5-en-2-mesylate.

PART B: PREPARATION OF 1-FLUORENYL-OMEGA-OCTENYL-2-MESYLATE

To a solution of 17.7 g (61 mmol) of 1-fluorenylhex-5-en-2-ol in 100 mL of methylene chloride, which also contains 13.91 mL (100 mmol) triethylamine, and which was at a temperature of about –40° to –50° C., was added 7.56 g (66 mmol) of mesyl chloride over a period of about 15 minutes. The resulting mixture was then stirred for about 15 minutes without further cooling. This mixture was then extracted with ice water, followed by cold 10 percent hydrochloric acid and cold sodium bicarbonate solution. The organic layer was then dried over Na₂SO₄ and the organic phase was removed to obtain 1-fluorenyl-oct-7-en-2-mesylate.

PART C: PREPARATION OF 1-FLUORENYL-OMEGA-DECENYL-2-MESYLATE

To a solution of 7.8 g (23.6 mmol) of 1-fluorenyl-dec-9-en-2-ol in 100 mL of methylene chloride, which also contains 7 mL (100 mmol) triethylamine, and which was at a temperature of about –40° to –50 ° C., was added 3.4 g (30 mmol) of mesyl chloride over a period of about 10 minutes. The resulting mixture was then stirred for about 30 minutes without further cooling. This mixture was then extracted with ice water, followed by cold 10 percent hydrochloric acid and cold sodium bicarbonate solution. The organic layer was then dried over Na₂SO₄ and the organic phase was removed to obtain 1-fluorenyl-dec-9-en-2-mesylate.

EXAMPLE FOUR: PREPARATION OF ORGANOOMEGA-ALKENYL-ORGANO COMPOUNDS

In this example, the 1-fluorenyl-omega-alkenyl-2-mesylates produced in Example Three, are quantitatively reacted with either indenyllithium or fluorenyllithium to form respectively 1-fluorenyl-omega-alkenyl-2-indenyl or 1-fluorenyl-omega-alkenyl-2-fluorenyl.

PART A: PREPARATION OF 1-FLUORENYL-OMEGA-HEXENYL-2-INDENYL 61 mmol indenyllithium, in 100 mL diethyl ether, is mixed with 1-fluorenyl-omega-hexenyl-2mesylate, at –78° C., and stirred overnight, at room temperature. The resulting mixture is then hydrolyzed with 50 mL water. The organic phase of this hydrolyzed mixture is then dried over Na₂SO₄ and then evaporated. The product, 1-fluorenyl-omega-hexenyl-2-indenyl (also known as "5-indenyl-6-fluorenyl-1-hexene" (compound 4A)) was obtained, which was a greenish oil, upon elution from column chromatography with pentane.

PART B: PREPARATION OF 1-FLUORENYL-OMEGA-OCTENYL-2-INDENYL 61 mmol indenyllithium, in 100 mL diethyl ether, is mixed with 1-fluorenyl-omega-octenyl-2-mesylate, at –78° C., and stirred overnight, at room temperature. The resulting mixture is then hydrolyzed with 50 mL water. The organic phase of this hydrolyzed mixture is then dried over $Na_2SO_4$ and then evaporated. The product 1-fluorenyl-omega-octenyl-2-indenyl (also known as "7-indenyl-8-fluorenyl-1-octene" (compound 4B)) was obtained, which was a greenish oil, upon elution from column chromatography with pentane.

PART C: PREPARATION OF 1-FLUORENYL-OMEGA-DECENYL-2-INDENYL 12.1 mmol indenyllithium, in 50 mL diethyl ether, is mixed with 1-fluorenyl-omega-decenyl-2-mesylate, at $-78°$ C., and stirred for four days, at room temperature. The resulting mixture is then hydrolyzed with 50 mL water. The organic phase of this hydrolyzed mixture is then dried over $Na_2SO_4$ and then evaporated. The product 1-fluorenyl-omega-decenyl-2-indenyl (also known as "9-indenyl-10-fluorenyl-1-decene" (compound 4C)) was obtained by crystallization in pentane at $-18°$ C.

PREPARATION OF 1-FLUORENYL-OMEGA-HEXENYL-2-FLUORENYL 61 mmol fluorenyllithium, in 100 mL diethyl ether, is mixed with 1-fluorenyl-omega-hexenyl-2-mesylate, at $-78°$ C., and stirred overnight, at room temperature. The resulting mixture is then hydrolyzed with 50 mL water. The organic phase of this hydrolyzed mixture is then dried over Na2SO4 and then evaporated. The product 1-fluorenyl-omega-hexenyl-2-fluorenyl (also known as "5,6-bis-fluorenyl-1-hexene" (compound 4D)) was obtained, which was a greenish oil, upon elution from column chromatography with pentane.

PART E: PREPARATION OF 1-FLUORENYL-OMEGA-OCTENYL-2FLUORENYL 61 mmol Fluorenyllithium, in 100 mL diethyl ether, is mixed with 1-fluorenyl-omega-octenyl-2-mesylate, at $-78°$ C., and stirred overnight, at room temperature. The resulting mixture is then hydrolyzed with 50 mL water. The organic phase of this hydrolyzed mixture is then dried over $Na_2SO_4$ and then evaporated. The product 1-fluorenyl-omega-octenyl-2-indenyl (also known as "7,8-bis-fluorenyl-1-octene" (compound 4E)) was obtained, which was a greenish oil, upon elution from column chromatography with pentane.

PART F: PREPARATION OF 1-FLUORENYL-OMEGA-DECENYL-2-FLUORENYL 12.1 mmol fluorenyllithium, in 50 mL diethyl ether, is mixed with 1-fluorenyl-omega-decenyl-2-mesylate, at $-78°$ C., and stirred for four days, at room temperature. The resulting mixture is then hydrolyzed with 50 mL water. The organic phase of this hydrolyzed mixture is then dried over $Na_2SO_4$ and then evaporated. The product 1-fluorenyl-omega-decenyl-2-fluorenyl (also known as "9,10-bis-fluorenyl-1-decene" (compound 4F)) was obtained by crystallization in pentane at $-18°$ C.

EXAMPLE FIVE: PREPARATION OF ORGANO-OMEGA-ALKENYL-ORGANO-TRANSITION-METAL COMPOUNDS AND THEIR USE

In this example, Compounds 4A-4F are formed into bridged metallocenes and use to polymerize ethylene.

PART A: PREPARATION OF BRIDGED METALLOCENES 1 g of each of compounds 4A-4F was dissolved in 40 mL diethyl ether and stirred with exactly 2 equivalents of η-butyllithium (1.6M in hexane) for at least 8 hours at room temperature. Then an amount of zirconium tetrachloride to provide one equivalent for each equivalent of the compounds 4A-4F is added and the mixture stirred overnight.

The reaction mixture was filtered over sodium sulfate. The residue on top of the sodium sulfate (complex+LiCl) was washed three times with 10 mL of pentane. The complex was then extracted with methylene chloride. The solvent was removed by evaporation. The zirconocene derivatives of compounds 4A-4F are identified as compounds 5A-5F, respectively.

PART B: PREPARATION OF METALLOCENE/ALUMINOXANE CATALYSTS

In a Schlenk tube compounds 5A-5F in toluene were reacted with methylaluminoxane and then exposed to an ethylene pressure of 0.4-0.6 bar. Incorporation of the resulting complex into a polymer chain is observed when the characteristic color of the complex is evident in precipitated polymer. When the solution becomes colorless in the presence of the precipitated polymer, the copolymerization capacity of the polymer chain is rated as 'very good'. Ratings of 'good' or 'poor' depend upon the changes observed in the hue of the solution. The results of these tests are given in the right hand column of Table I.

PART C: POLYMERIZATION WITH METALLOCENE/ALUMINOXANE CATALYSTS

To a Buechi laboratory autoclave, 1L, is added 500 mL pentane and 7 mL MAO solution followed by toluene solution containing a known quantity of the complexes prepared in Example 5B. A constant ethylene pressure of 10 bar was applied for 1 hour. The polymerization was conducted at 60° C. at 800 rpm. Tables I summarizes the results.

TABLE I

| Complex Number | Amount, $10^{-6}$ mol | Polymer Recovered, grams | Activity, g PE (g Zr × hr × $10^5$ Pa) | Copolymerization Capacity |
|---|---|---|---|---|
| 5A | 1.9 | 22 | 12,600 (61.1)[b] | Good |
| 5B | 1.8 | 17 | 10,300 (59.7) | Very Good |
| 5C | 2.0 | 36 | 19000 (61.7) | Very Good |
| 5D | 0.4 | 65 | 163,000 (74.0) | Good |
| 5E | 0.6 | 100[a] | 366,000 (94.0) | Very Good |
| 5F | 1.6 | 77[a] | 318000 (85.0) | Very Good |

[a]Duration of polymerization 0.5 hour for 5E and 10 minutes for 5F;
[b]Maximum interior temperature of polymerization reactor; °C.

Self-immobilization occurs to the greatest extent with complexes having the longest omega-alkenyl substituents. An omega-alkenyl substituent of greater than four carbon atoms appears favorable for self-immobilization of the fluorenyl-indenyl bridged zirconocenes.

The most active zirconocenes for the polymerization of ethylene are those having omega-alkenyl substitution of the ethylidene-bis(fluorenyl) structure, compounds 5C and 5D with activities of 163,000 and 366,000 grams polyethylene per gram of zirconium per hour per bar ($1 \times 10^5$ Pa) respectively. The molecular weight of the resulting ethylene polymers is nearly twice that obtained with the following two compounds. As shown in Table I replacement of one of the fluorenyl groups with indenyl, compounds 5A and 5B, decreases polymerization activity to 12,600 and 10,300 g PE/(g Zr per hour per bar) respectively, under the polymerization conditions used.

That which is claimed:

1. A process to produce an ethylene-bridged-metallocene-transition-metal compound that has an omega-alkenyl substitution on said ethylene bridge, said process comprising:
   (a) contacting a diolefin compound with a peracid compound to form an omega-alkenyl oxirane compound;
   (b) contacting said omega-alkenyl oxirane compound with an organometal compound to form an organo-omega-alkenyl-alcohol compound;
   (c) contacting said organo-omega-alkenyl-alcohol compound with an organosulfur compound to form an organo-omega-alkenyl organosulfur ester compound;
   (d) contacting said organo-omega-alkenyl-organosulfur ester compound with an organometal compound to form an organo-omega-alkenyl-organo compound; and
   (e) contacting said organo-omega-alkenyl-organo compound with a transition metal compound to form an ethylene-bridged-metallocene-transition-metal compound that has an omega-alkenyl substitution on said ethylene bridge.

2. A process according to claim 1 wherein said diolefin compound is selected from the group consisting of 1,3 butadiene, 1,4 pentadiene, 1,5 hexadiene, 1,6 heptadiene, 1,7 octadiene, 1,8 nonadiene, 1,9 decadiene, and 5-methyl-1,7-octadiene, and mixtures thereof.

3. A process according to claim 1 wherein said peracid compound is meta-chloroperbenzoic acid.

4. A process according to claim 1 wherein said organometal compound in step (b) is substituted with an organo-radical selected from the group consisting of unsubstituted or substituted cyclopentadienyl radicals, unsubstituted or substituted indenyl radicals, unsubstituted or substituted fluorenyl radicals, and unsubstituted or substituted tetrahydroindenyl radicals, and mixtures thereof.

5. A process according to claim 1 wherein said organosulfur compound in step (c) is selected from the group consisting of methanesulfonyl chloride, trifluoromethanesulfonyl chloride, and mixtures thereof.

6. A process according to claim 1 wherein said organometal compound in step (d) is substituted with an organo-radical selected from the group consisting of unsubstituted or substituted cyclopentadienyl radicals, unsubstituted or substituted indenyl radicals, unsubstituted or substituted fluorenyl radicals, and unsubstituted or substituted tetrahydroindenyl radicals, and mixtures thereof.

7. A process according to claim 1 wherein said transition metal compound in step (e) is selected from the group consisting of vanadium dichloride, vanadium trichloride, vanadium tetrachloride, vanadium pentafluoride, vanadium triiodide, titanium dibromide, titanium tetrachloride, titanium trichloride, titanium tetrafluoride, titanium tetraiodide, titanium tetrabromide, zirconium trichloride, zirconium tetrachloride, zirconium tetrabromide, zirconium tetraiodide, zirconium tetrafluoride, $Zr(NH_2)_4$, $Zr(N(CH_2CH_3)_2)_4$, $Zr(N(CH_2CH_3)_2)_2Cl_2$, hafnium trichloride, hafnium tetrachloride, hafnium tetrabromide, hafnium tetraiodide, hafnium tetrafluoride, $Hf(NH_2)_4$, $Hf(N(CH_2CH_3)_2)_4$, $Hf(N(CH_2CH_3)_2)_2Cl_2$, chromic chloride, titanium tetraethoxide, titanium tetrabutoxide, zirconium tetrabutoxide, dicyclopentadienyl titanium dichloride, dicyclopentadienyl zirconium dichloride, and mixtures thereof.

8. A process to polymerize olefins using an ethylene-bridged-metallocene-transition-metal compound that has an omega-alkenyl substitution on said ethylene bridge, said process comprising contacting said ethylene-bridged-metallocene-transition-metal compound that has an omega-alkenyl substitution on said ethylene bridge, with olefins under polymerization conditions, where said ethylene-bridged-metallocene-transition-metal compound that has an omega-alkenyl substitution on said ethylene bridge has been prepared by the reaction process of claim 1.

9. A process according to claim 8 wherein said olefins are selected from the group consisting of ethylene, propylene, 1-butene, 3-methyl1-butene, 3-methyl-1-pentene, 3ethyl-1-hexene, 1-hexene, 4-methyl-1-pentene, 1-octene, 1-hexadecene, cyclopentene, norbornene, styrene, 4-methyl styrene, vinyl cyclohexane, butadiene, and mixtures thereof.

10. A process according to claim 8 wherein said contacting is conducted under slurry polymerization conditions.

* * * * *